United States Patent
Hiles et al.

(10) Patent No.: US 6,187,039 B1
(45) Date of Patent: Feb. 13, 2001

(54) TUBULAR SUBMUCOSAL GRAFT CONSTRUCTS

(75) Inventors: Michael C. Hiles, Lafayette; Umesh H. Patel, West Lafayette; Leslie A. Geddes, West Lafayette; Stephen F. Badylak, West Lafayette, all of IN (US)

(73) Assignee: Purdue Research Foundation, West Lafayette, IN (US)

( * ) Notice: Under 35 U.S.C. 154(b), the term of this patent shall be extended for 0 days.

(21) Appl. No.: 09/297,620

(22) PCT Filed: Dec. 10, 1997

(86) PCT No.: PCT/US97/22040
§ 371 Date: May 4, 1999
§ 102(e) Date: May 4, 1999

(87) PCT Pub. No.: WO98/25543
PCT Pub. Date: Jun. 18, 1998

Related U.S. Application Data
(60) Provisional application No. 60/032,679, filed on Dec. 10, 1996.

(51) Int. Cl.⁷ .................................................. A60F 2/06
(52) U.S. Cl. ..................................... 623/1.44; 148/1.41
(58) Field of Search .................. 623/1.44, 1.48, 623/1.41

(56) References Cited

U.S. PATENT DOCUMENTS

| | | |
|---|---|---|
| 2,127,903 | 8/1938 | Bowen . |
| 3,562,820 | 2/1971 | Braun . |
| 5,281,422 * | 1/1994 | Naughton et al. ............... 435/1 |
| 5,443,950 * | 8/1995 | Naughton et al. ............... 435/1 |
| 5,693,085 * | 12/1997 | Buirge et al. .................... 623/1 |
| 5,873,904 * | 2/1999 | Ragheb et al. ................... 623/1 |
| 5,876,448 * | 3/1999 | Thompson et al. ............. 623/12 |
| 5,922,028 * | 7/1999 | Plouhar et al. ................. 623/13 |

* cited by examiner

Primary Examiner—Michael Milano
Assistant Examiner—Hieu Phan
(74) Attorney, Agent, or Firm—Barnes & Thornburg (57) ABSTRACT

An easy-to-produce and mechanically strong tube of an implantable submucosal tissue has been developed which is manufactured in any desired length, wall thickness, or diameter. The construct produced by the method of the invention may be used as grafts for arteries, veins, ureters, urethras, shunts, or in any application where a compliant, tissue-compatible tube is needed. The manufacture of the submucosal tissue prosthesis generally involves wrapping a first sheet of submucosal tissue (60) and a second sheet of submucosal tissue (70) around a mandrel (50), wherein the first end (74) and the second opposite end (76) of the second sheet of submucosal tissue (70) are sutured together with sutures (78). The submucosal tissue is compressed and dried on the mandrel (50) before removing the construct by pulling on a first end (54) and a second end (56) of a water permeable tape to unwind the tape and thus release the construct for eventual use.

37 Claims, 2 Drawing Sheets

TUBULAR SUBMUCOSAL GRAFT CONSTRUCTS

CROSS-REFERENCES TO RELATED APPLICATIONS

This application is a U.S. national application of international application Ser. No. PCT/US97/22040 filed Dec. 10, 1997, which claims priority to U.S. provisional application Ser. No. 60/032,679 filed Dec. 10, 1996.

TECHNICAL FIELD

This invention relates to implantable biological tissue graft constructs suitable for various medical applications and the process for producing such graft constructs. More specifically, submucosal tissue is used to form tubular multi-laminate constructs of varying diameter. The tissue graft constructs have applications as arterial and venous grafts, ureter and urethra replacements, and as various ducts and shunts.

BACKGROUND OF THE INVENTION

Researchers in the surgical arts have been working for many years to develop new techniques and materials for use as grafts to replace or repair damaged or diseased tissue structures, particularly bones and connective tissues, such as ligaments and tendons, and to hasten fracture healing. It is very common today, for instance, for an orthopedic surgeon to harvest a patellar tendon of autogenous or allogenous origin for use as a replacement for a torn cruciate ligament. The surgical methods for such techniques are well known. Further, it has become common for surgeons to use implantable prostheses formed from plastic, metal and/or ceramic materials for reconstruction or replacement of physiological structures. Yet, despite their wide use, presently available surgically implanted prostheses present many attendant risks to the patient. Therefore, surgeons are in need of a non-immunogenic, high tensile strength graft material which can be used for the surgical repair of bone, tendons, ligaments and other functional tissue structures.

More recently researchers have been working to develop biological tissues for use as implants and for use in the repair of damaged or diseased tissues, since plastic and polymer materials have drawbacks in these medical applications. While plastics and polymers may have some desirable mechanical properties (e.g., tensile strength), plastics have been found to become infected and in vascular applications plastics have been reported as inducing thrombogenesis.

Tubular prostheses made from natural tissues have been widely used in recent years in the surgical repair and replacement of diseased or damaged blood vessels in human patients. Natural tissue prostheses fall into three general classes: Autogenous, homologous, and heterologous prostheses. Autogenous material tissue prostheses are prepared from tissues taken from the patient's own body (e.g., saphenous vein grafts). Use of such prostheses eliminates the possibility of rejection of the implanted prosthesis, but requires a more extensive and time-consuming surgical intervention with attendant risks to the patient. Homologous natural tissue prostheses are prepared from tissue taken from another human, while heterologous natural tissue prostheses are prepared from tissue taken from a different species. The use of homologous and heterologous umbilical cord vessels as, e.g., vascular and ureteral prostheses are disclosed in U.S. Pat. Nos. 3,894,530; 3,974,526; and 3,988,782.

In addition, autogenous vascular prostheses prepared from sheets of pericardial tissue have been disclosed by Yoshio Sako, "Prevention of Dilation in Autogenous Venous and Pericardial Grafts in the Thoracic Aorta," Surgery, 30, pp. 148–160 (1951) and by Robert G. Allen and Francis H. Cole, Jr., "Modified Blalock Shunts Utilizing Pericardial Tube Grafts," Jour. Pediatr. Surg., 12(3), pp. 287–294 (1977). Heterologous vascular prostheses prepared from sheets of porcine pericardial tissue have been disclosed by Ornvold K. et al., "Structural Changes of Stabilized Porcine Pericardium after Experimental and Clinical Implantation," in Proc. Eur. Soc. for Artif Organs, Vol. VI, Geneva, Switzerland (1979).

The necessary characteristics of a tubular vascular prosthesis are biological compatibility, adequate strength, resistance to infection, resistance to biological degradation, non-thrombogenicity and lack of aneurysm formation. As used in this application, the term biological compatibility means that the prosthesis is non-toxic in the in vivo environment of its intended use, and is not rejected by the patient's physiological system (i.e., is non-antigenic). Furthermore, it is desirable that the prosthesis be capable of production at an economical cost in a wide variety of lengths, diameters and shapes (e.g., straight, curved, bifurcated), be readily anastomosed to the patient's body and to other tubular prostheses of the same or different type, and exhibit dimensional stability in use.

As disclosed in U.S. Pat. No. 4,902,508, vascular grafts constructs comprising intestinal submucosal tissue have been previously described and utilized to replace damaged or diseased vascular tissues. The vascular graft constructs were prepared by inserting a glass rod of the appropriate diameter into the lumen of the submucosal tissue and hand-suturing along the seam of the submucosal tissue. The submucosal tissue vascular grafts are aseptically fabricated during surgery and typically take a surgeon about one half hour to prepare. Therefore to avoid spending time preparing the graft constructs during surgery, premade, presterilized grafts of different diameters are desirable.

Preparation of a tubular prosthesis of the correct length and shape increases the ease of implantation and enhances the functionality of the implant. For example, a tubular prosthesis that is too long for the intended application may kink after implantation, whereas implantation of a prosthesis that is too short places excessive tension on the anastomoses at its ends, thereby resulting in trauma to said anastomoses. Thus, it would be highly desirable to provide an array of tubular prosthesis that vary in diameter and that can be cut transversely to a desired length at any point between its ends without otherwise substantially damaging the prosthesis.

The present invention is directed to a tubular prosthesis comprising submucosal tissue and methods for preparing such a prosthesis. Submucosal tissue, prepared in accordance with the present invention, has been previously described as a biocompatible, non-thrombogenic graft material that enhances the repair of damaged or diseased host tissues. Numerous studies have shown that warm-blooded vertebrate submucosa is capable of inducing host tissue proliferation, remodeling and regeneration of tissue structures following implantation in a number of in vivo microenvironments including lower urinary tract, body wall, tendon, ligament, bone, cardiovascular tissues and the central nervous system. Upon implantation, cellular infiltration and a rapid neovascularization are observed and the submucosa material is remodeled into host replacement tissue with site-specific structural and functional properties.

Submucosal tissue can be obtained from various tissue sources, harvested from animals raised for meat production, including, for example, pigs, cattle and sheep or other warm-blooded vertebrates. More particularly, the submucosa is isolated from a variety of tissue sources including the alimentary, respiratory, intestinal, urinary or genital tracts of warm-blooded vertebrates. In general, submucosa is prepared from these tissue sources by delaminating the submucosal from both the smooth muscle layers and the mucosal layers. The preparation of intestinal submucosa is described and claimed in U.S. Pat. No. 4,902,508, the disclosure of which is expressly incorporated herein by reference. Urinary bladder submucosa and its preparation is described in U.S. Pat. No. 5,554,389, the disclosure of which is expressly incorporated herein by reference. Stomach submucosa has also been obtained and characterized using similar tissue processing techniques. Such is described in U.S. patent application Ser. No. 60/032,683 titled STOMACH SUBMUCOSA DERIVED TISSUE GRAFT, filed on Dec. 10, 1996. Briefly, stomach submucosa is prepared from a segment of stomach in a procedure similar to the preparation of intestinal submucosa. A segment of stomach tissue is first subjected to abrasion using a longitudinal wiping motion to remove the outer layers (particularly the smooth muscle layers) and the luminal portions of the tunica mucosa layers. The resulting submucosa tissue has a thickness of about 100 to about 200 micrometers, and consists primarily (greater than 98%) of acellular, eosinophilic staining (H&E stain) extracellular matrix material.

SUMMARY OF THE INVENTION

In accordance with the present invention, an implantable tubular prosthesis comprising submucosal tissue is prepared in the shape of a tube. The tubular construct comprises a first sheet of submucosal tissue rolled into the shape of a multi-layered tube of submucosal tissue and a second sheet of submucosal tissue that is wrapped around the tube of submucosal tissue. The second sheet of submucosal tissue is overlaid onto the tube of submucosal tissue so that a first edge is in contact with the submucosa tissue and the second opposite edge is either sutured to the first edge or extends over the first edge and is sutured to the second sheet of submucosal tissue. The multi-layered tubular graft constructs of the present invention are formed to have fluid-tight seams and can be shaped to match the endogenous tissue to be replaced by the graft construct.

Further in accordance with the present invention, a process is provided for producing an implantable tissue graft construct formed in the shape of a tube having a seam extending longitudinally along the length of the graft wherein the seam has been sealed to resist movement of fluids from the lumen through the seam to the exterior of the tube. One method of forming the submucosal tubular constructs of the present invention comprises the steps of:

A. overlaying a sheet of submucosal tissue around the circumference of a mandrel to form a tube of submucosal tissue having a multi-layered overlapped region;

B. fixing the submucosal tissue layers in the overlapped region to one another;

C. overlaying a second sheet of submucosal tissue onto the tube of submucosal tissue to form a second tube of submucosal tissue wherein the seam of the second tube of submucosal tissue is sealed by sutures; and D. compressing the overlaid layers of submucosal tissue under dehydrating conditions.

The present invention allows for the construction of multi-layered tubular graft constructs from sheets of submucosal tissue wherein the walls of the formed tubular prosthesis do not contain any perforations that provide a direct passageway from the lumen of the tube to the exterior surface. The multi-layered tubular prosthesis of the have sufficient strength and durability to be use in vascular applications without leakage or failure of the tubular prosthesis.

BRIEF DESCRIPTION OF THE DRAWING

The invention will be further described in connection with the attached. drawing figures showing preferred embodiments of the invention including specific parts and arrangements of parts. It is intended that the drawings included as a part of this specification be illustrative of the preferred embodiments of the present invention and should in no way be considered as a limitation on the scope of the invention.

DETAILED DESCRIPTION OF THE PREFERRED EMBODIMENTS

In many medical applications an implantable biological tissue tubular prosthesis is desirable. The present invention provides an arbitrary length, arbitrary diameter, multi-layer biological tissue graft construct. The product can be manipulated to suit various medical applications where a tubular construct or conduit is desired. Examples of possible applications are arterial and venous grafts, ureter and urethra replacements, and various ducts and shunts. The process of fabricating the tubular constructs of the present invention involves preparing a sheet of submucosal tissue in accordance with U.S. Pat. No. 4,902,508, and overlaying the tissue around a mandrel of the appropriate diameter to form a tube of submucosal tissue. The sheet of submucosal tissue can be wrapped around the mandrel multiple times, to form a multi-layered tube of submucosal tissue. A second sheet of submucosal tissue is then wrapped around the circumference of the formed tube of submucosal tissue and the end of the second sheet of submucosal tissue is sutured to the graft construct to form a water tight seam that extends longitudinally along the length of the tube. The submucosal tissue is then compressed under dehydrating conditions, and optionally heated, to produce the unitary tubular prosthesis of the present invention.

Submucosal tissue suitable for use in the formation of the present graft constructs comprises naturally associated extracellular matrix proteins, glycoproteins and other factors. More particularly, the submucosal tissues for use in accordance with this invention include intestinal submucosa, stomach submucosa, urinary bladder submucosa, and uterine submucosa. Intestinal submucosal tissue is one preferred material, and more particularly small intestinal submucosa.

Suitable intestinal submucosal tissue typically comprises the tunica submucosa delaminated from both the tunica muscularis and at least the luminal portion of the tunica mucosa. In one embodiment of the present invention the intestinal submucosal tissue comprises the tunica submucosa and basilar portions of the tunica mucosa including the lamina muscularis mucosa and the stratum compactum which layers are known to vary in thickness and in definition dependent on the source vertebrate species.

The preparation of intestinal submucosal tissue for use in accordance with this invention is described in U.S. Pat. No. 4,902,508. A segment of vertebrate intestine, preferably harvested from porcine, ovine or bovine species, but not excluding other species, is subjected to abrasion using a longitudinal wiping motion to remove the outer layers, comprising smooth muscle tissues, and the innermost layer, i.e., the luminal portion of the tunica mucosa. The submucosal tissue is rinsed with saline and optionally sterilized.

As a tissue graft, submucosal tissue undergoes remodeling and induces the growth of endogenous tissues upon implantation into a host. It has been used successfully in vascular grafts, urinary bladder and hernia repair, replacement and repair of tendons and ligaments, and dermal grafts. When used in such applications the graft constructs appear not only to serve as a matrix for the regrowth of the tissues replaced by the graft constructs, but also promote or induce such regrowth of endogenous tissue. Common events to this remodeling process include: widespread and very rapid neovascularization, proliferation of granulation mesenchymal cells, biodegradation/resorption of implanted intestinal submucosal tissue material, and lack of immune rejection.

The tubular submucosal tissue graft constructs of the present invention can be sterilized using conventional sterilization techniques including glutaraldehyde tanning, formaldehyde tanning at acidic pH, propylene oxide or ethylene oxide treatment, gas plasma sterilization, gamma radiation, electron beam radiation, peracetic acid sterilization. Sterilization techniques which do not adversely affect the mechanical strength, structure, and biotropic properties of the submucosal tissue is preferred. For instance, strong gamma radiation may cause loss of strength of the sheets of submucosal tissue. Preferred sterilization techniques include exposing the graft to peracetic acid, 1–4 Mrads gamma irradiation (more preferably 1–2.5 Mrads of gamma irradiation), ethylene oxide treatment or gas plasma sterilization; peracetic acid sterilization is the most preferred sterilization method. Typically, the submucosal tissue is subjected to two or more sterilization processes. After the submucosal tissue is sterilized, for example by chemical treatment, the tissue may be wrapped in a plastic or foil wrap and sterilized again using electron beam or gamma irradiation sterilization techniques.

Submucosal tissue can be stored in a hydrated or dehydrated state. Lyophilized or air dried submucosa tissue can be rehydrated and used in accordance with this invention without significant loss of its biotropic and mechanical properties.

The sheets of submucosal tissue can be conditioned, as described in U.S. Pat. No. 5,275,826 (the disclosure of which is expressly incorporated herein by reference) to alter the viscoelastic properties of the submucosal tissue. In accordance with one embodiment submucosa delaminated from the tunica muscularis and luminal portion of the tunica mucosa is conditioned to have a strain of no more than 20%. The submucosal tissue is conditioned by stretching, chemically treating, enzymatically treating or exposing the tissue to other environmental factors. In one embodiment the strips of intestinal submucosa tissue are conditioned by stretching in a longitudinal or lateral direction so that the strips of intestinal submucosa tissue have a strain of no more than 20%.

In one embodiment the submucosal tissue is conditioned by stretching the graft material longitudinally to a length longer than the length of the submucosal tissue from which the graft construct was formed. One method of conditioning the tissue by stretching involves application of a given load to the submucosa for three to five cycles. Each cycle consists of applying a load to the graft material for five seconds, followed by a ten second relaxation phase. Three to five cycles produces a stretch-conditioned graft material with reduced strain. The graft material does not immediately return to its original size; it remains in a "stretched" dimension. Optionally, the graft material can be preconditioned by stretching in the lateral dimension.

In one embodiment the submucosal tissue is stretched using 50% of the predicted ultimate load. The "ultimate load" is the maximum load that can be applied to the submucosal tissue without resulting in failure of the tissue (i.e. the break point of the tissue). Ultimate load can be predicted for a given strip of submucosal tissue based on the source and thickness of the material. Accordingly, one method of conditioning the tissue by stretching involves application of 50% of the predicted ultimate load to the submucosa for three to ten cycles. Each cycle consists of applying a load to the graft material for five seconds, followed by a ten second relaxation phase. The resulting conditioned submucosal tissue has a strain of less than 30%, more typically a strain from about 20% to about 28%. In one preferred embodiment conditioned the submucosal tissue has a strain of no more than 20%. The term strain as used herein refers to the maximum amount of tissue elongation before failure of the tissue, when the tissue is stretched under an applied load. It is expressed as a percentage of the length of the tissue before loading. The conditioned submucosal strips can be used to form the tubular construct or alternatively the tubular construct can be conditioned after its formation.

The tubular graft constructs of the present invention are formed as a multilaminate construct wherein a first sheet of submucosal tissue is formed into the shape of a tube of submucosal tissue and a second sheet is overlaid onto the tube of submucosal tissue. The dimensions of the individual sheets of submucosal tissue used is not critical and the term "sheet of submucosal tissue" is defined herein to include submucosal tissue from one or more vertebrate sources or organs in a wide variety of sizes and shapes. After the second sheet of submucosal tissue has been layered onto the mandrel, pressure is applied to the overlapped portions to compress the submucosal against the mandrel. In preferred embodiments the mandrel surfaces is water permeable. The term "water permeable surface" as used herein includes surfaces that are water absorbent, microporous or macroporous. Macroporous materials include perforated plates or meshes made of plastic, metal, ceramics or wood.

In one preferred embodiment the multiple layers of submucosal tissue are compressed under dehydrating conditions. The term "dehydrating conditions" is defined to include any mechanical or environmental condition which promotes or induces the removal of water from the submucosal tissue. To promote dehydration of the compressed submucosal tissue, at least one of the two surfaces compressing the tissue is water permeable. Dehydration of the tissue can optionally be further enhanced by applying blotting material, heating the tissue or blowing air across the exterior of the compressing surfaces.

Submucosal tissue typically has an abluminal and a luminal surface. The luminal surface is the submucosal surface facing the lumen of the organ source and typically adjacent to an inner mucosa layer in vivo whereas the abluminal surface is the submucosal surface facing away from the lumen of the organ source and typically in contact with smooth muscle tissue in vivo. In one embodiment one or more sheets of submucosal tissue are wrapped onto the mandrel with the luminal surface of the submucosal tissue in contact with the mandrel surface. Thus the luminal surface of the sheet of submucosal tissue faces the lumen of the formed tube of submucosal tissue. However the tube of submucosa tissue can also be formed from one or more sheets of submucosal tissue with the abluminal surface facing the lumen of the formed tubular graft construct.

In accordance with one embodiment a tubular prosthesis is manufactured comprising a first sheet of submucosal tissue formed in the shape of a tube of submucosal tissue, and a second sheet of submucosal tissue circumferentially wrapped around and in adherent contact with the tube of submucosal tissue, wherein the seam formed by the end piece of the second sheet of submucosal tissue is sutured to form a water tight seal. The tube of submucosal tissue comprises the first sheet of submucosal tissue, having a first edge and a second opposite edge, formed in the shape of a tube wherein the second opposite edge of the first sheet extends over the first edge of the first sheet to define a multiple layered overlapped region of submucosal tissue. As used herein the term "overlapped region" refers to the portion of the multi-layered tube defined by an overlap angle (θ) that extends between the first and second edges of the first sheet of submucosal tissue formed as a tube (See FIG. 5b). The submucosal tissue layers in the overlapped region are fixed to one another using standard techniques known to those skilled in the art. Alternatively the submucosal tissue layers can be fixed to one another by treating the tissue with glutaraldehyde and "vacuum pressing" the overlapped tissue layers, as described below.

In one embodiment the multiple layers of submucosal tissue in the overlapped region are fixed to one another by treatment with a crosslinking agent, for example an aldehyde such as formaldehyde or more preferably glutaraldehyde. In one embodiment the seam formed in the tube of submucosal tissue can be "spot welded" to ensure that the end piece does not come loose. In accordance with this embodiment, a Q-tip, moistened with χ% glutaraldehyde (or other cross linking or adhesive agent), is wiped along the overlapped region forming the seam. The value for χ is about 0.1 to about 1.0%, more probably about 0.5%, but there is a relationship between the seam width, the glutaraldehyde concentration and number of turns that determines the bursting pressure. In one embodiment the entire graft construct can be immersed into a dilute solution of glutaraldehyde (comprising about 0.1 to about 1.0% glutaraldehyde) and then compressed under dehydrating conditions to fix the multiple layers of the tube of submucosal tissue to one another. In addition, the multiple layers of submucosal tissue in the overlapped region can be sutured to one another, and in one embodiment the layers of the overlapped region are fixed with sutures in the absence of treatment with a crosslinking agent.

Figures 1, 2, 3:
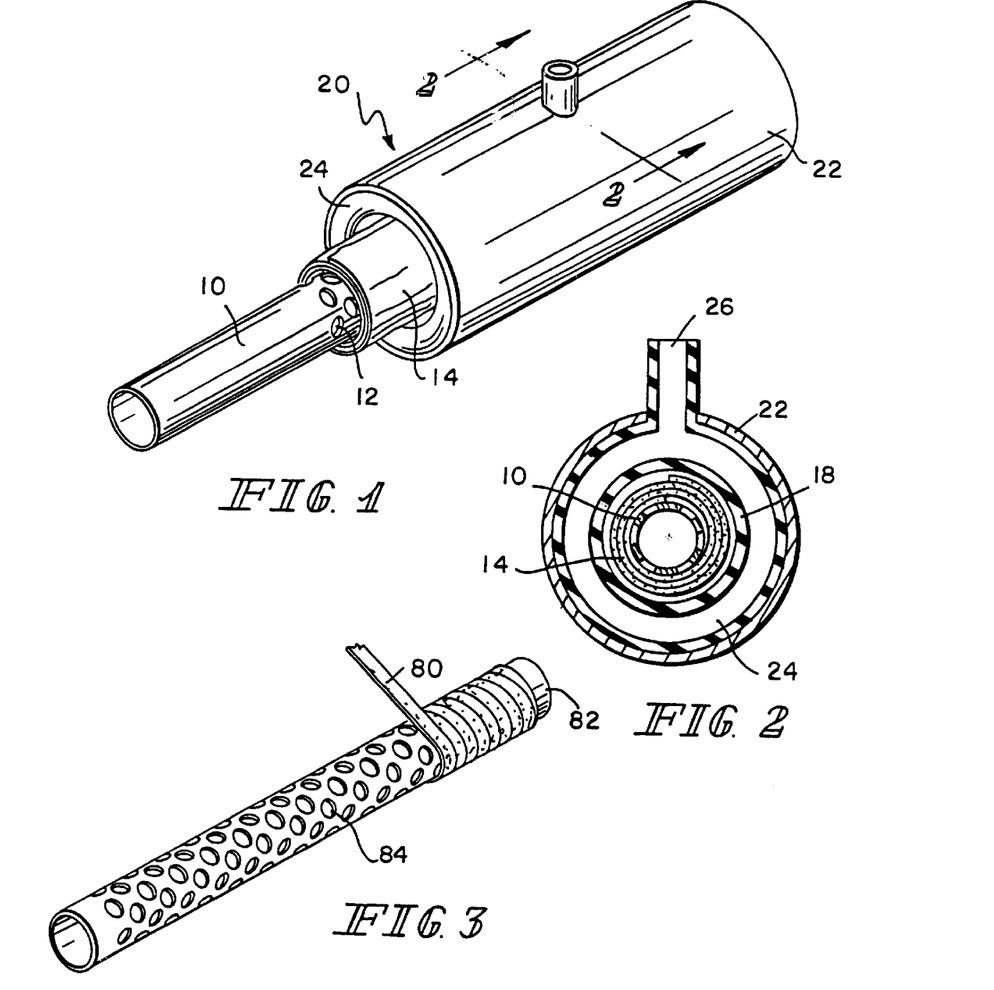
FIG. 1 is a perspective view of a compression chamber with a submucosal tissue covered mandrel inserted into the lumen of the compression chamber.
FIG. 2 is a sectional view of the compression chamber of claim 1.
FIG. 3 is a perspective view of a single strip of submucosal tissue helically wound around a mandrel.
Figures 5A, 5B, 5C:
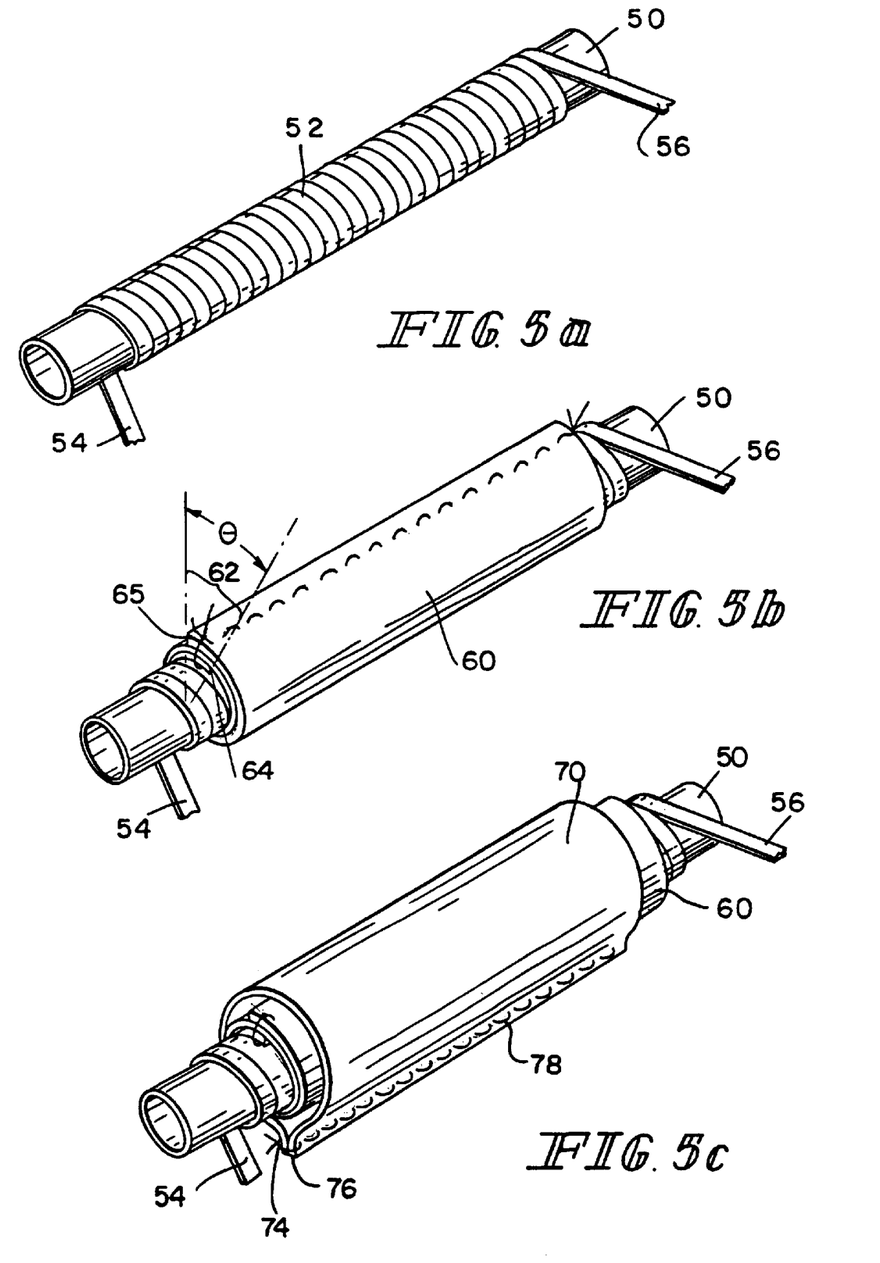
FIG. 5a is a perspective view of a single strip of water permeable material wound around a multihole mandrel.
FIG. 5b is a perspective view of a multihole mandrel having been wrapped with a single strip of water permeable material, and a first sheet of submucosal tissue.
FIG. 5c is a perspective view of a multihole mandrel having been wrapped with a single strip of water permeable material, a first sheet of submucosal tissue and a second sheet of submucosal tissue.

In one preferred embodiment, the tube of submucosal tissue formed by the first sheet of submucosal tissue, is formed such that the first and second opposite edges of the first sheet of submucosal tissue are substantially parallel to one another as shown in FIG. 1 and FIG. 5b. In this embodiment the sheet of submucosal tissue is rolled into the shape of a tube having multiple layers. Typically the tube of submucosal tissue comprises two layers of submucosal tissue and the multiple overlapped region comprises three layers of submucosal tissue.

The graft constructs of the present invention further comprise a second sheet of submucosal tissue wherein the second sheet is in adherent contact with the exterior surface of the tube of submucosal tissue. In one embodiment, the first and second opposite edges of the second sheet of submucosal tissue are sutured together along the length of the tube of submucosal tissue without perforating the underlying tube of submucosal tissue. In an alternative embodiment, the second opposite edge of the second sheet extends over the first edge of the second sheet and is sutured to the second sheet of submucosal tissue without perforating the underlying tube of submucosal tissue.

In preferred embodiments the overlapped region of the tube of submucosal tissue is offset from the sutures formed in the second sheet of submucosal tissue (i.e. the overlapped region does not contact the sutured region of the second sheet). In one embodiment the sutures formed in the second sheet of submucosal tissue are situated 90–180° along the circumference of the tube of submucosal tissue in relation to the overlapped region, and in one embodiment the sutures are located 180° along the circumference of the tube of submucosal tissue in relation to the overlapped region (See FIG. 5c).

In accordance with one embodiment, the tubular prosthesis comprises a first sheet of submucosal tissue, having first and second edges that are substantially parallel to each other, rolled into the shape of a multi-layered tube having an overlapped region wherein the first and second edges remain substantially parallel to one another in the formed tube and the layers of the overlapped region are fixed to one another with sutures or by exposure to a crosslinking agent. The tubular construct further comprises a second sheet of submucosal tissue adhered to the exterior surface of the formed tube of submucosal tissue, wherein the second sheet, having first and second edges that are substantially parallel to each other, is wrapped circumferentially around the tube of submucosal tissue and the first and second edges are fixed to one another with sutures.

In accordance with one embodiment the tubular prosthesis of the present invention is formed by the following steps: A mandrel is selected having a diameter matching the preferred diameter of the final construct. The mandrel is typically cylindrical in shape and in preferred embodiments comprises a hollow tube that is water permeable. A first sheet of submucosal tissue, having a first edge and a second opposite edge, is then overlaid onto the mandrel to form a tube of submucosal tissue, wherein the second opposite edge of the first sheet of submucosal tissue extends over the first edge of the first sheet of submucosal tissue to define a multi-layered overlapped region of submucosal tissue. The submucosal tissue layers in the overlapped region are then fixed to one another to form a seam that extends longitudinally along the length of the formed tube. A second sheet of submucosal tissue, having a first edge and a second opposite edge is then overlaid onto the tube of submucosal tissue and the second opposite edge of the second sheet of submucosal tissue is sutured to the overlaid second sheet of submucosal tissue along the length of the tube of submucosal tissue without perforating the tube of submucosal tissue. In one embodiment the first and second edges of the second sheet of submucosa tissue are sutured together to form a single layered second tube that encompasses the first tube of submucosal tissue. The layers of submucosal tissue are then compressed against the mandrel under dehydrating conditions.

The invention will be further described with respect to preferred embodiments as illustrated in the drawing figures. Referring to FIG. 1, one preferred embodiment of a mandrel 10 for wrapping biological tissue sheets is illustrated. The mandrel 10 is a hollow metal or plastic tube comprising holes 12 in the wall of the tube along a portion of, or, alternatively, along the entire length of the metal tube. The size of the holes in the mandrel 10 is not critical provided the mandrel is sufficiently porous to allow dehydration of the submucosal tissue upon compression of the wrapped submucosal tissue 14. In one preferred embodiment the mandrel is a metal tube, and more preferably, the metal tube is composed of aluminum. Submucosal tissue 14 is overlaid onto the mandrel 10 to form a multi-layered tube of submucosal tissue. The submucosal tissue covered mandrel is then inserted into the lumenal space of a compression chamber 20 that is utilize in one embodiment to prepared the tubular constructs of the present invention. The compression chamber 20 comprises outer shell 22, a bladder 24 and pressure port 26. The bladder 24 may be attached or adhered to the inner wall of outer shell 22 by various techniques, e.g., with an adhesive or heat bonding. As shown in FIG. 2, the wrapped mandrel 10 is inserted into compression chamber 20 where the inner membrane 18 of bladder 24 contacts and compress the submucosal tissue 14 when a fluid is delivered into pressure port 26 to inflate the bladder 24. Bladder 24 is inflated to the desired pressure and the pressure is maintained until the submucosa tissue has been sufficiently dehydrated.

Optionally, the compression and drying process may be augmented with low temperature heating (e.g., less than about 50° C.) of the tissue graft construct. Further, air or an inert gas (e.g., $N_2$) may be passed through the lumen of the mandrel as an alternative or conjunctive means to augment the drying process. The air/gas drawn through the lumen can optionally be heated to further speed the dehydration process. The holes 12 formed in the walls of mandrel 10 aid in the drying process of submucosal tissue 14, however, this structure merely represents one embodiment of a mandrel suitable for use in accordance with the present invention (See FIG. 1). The mandrel can also be formed as a solid cylinder or as a tube that lacks holes. In one embodiment the mandrel comprises a hollow tube with holes formed in the walls of the mandrel, and the compression of the submucosal tissue is assisted by drawing a vacuum on the lumen of the mandrel.

Figure 4:
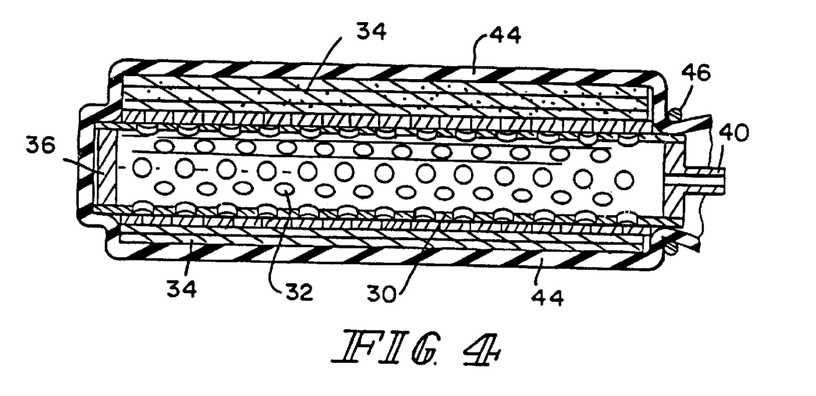
FIG. 4 is a sectional view of the submucosal covered mandrel wherein one end of the mandrel has been sealed and a vacuum is pulled on the opened end.

Alternatively, the compression of the submucosal tissue may be achieved by continuously rolling the mandrel containing the wrapped biological tissue sheets in direct contact with another surface to provide a direct compression force. In addition, in one preferred embodiment, as shown in FIG. 4, the application of a vacuum can provide the sole compressing force for compressing the overlapped portions of the multiple strips of submucosal tissue (vacuum pressing). In this embodiment a mandrel 30, formed as a hollow tube having a plurality of holes 32 formed in the wall of the mandrel 30 is covered with multiple layers of submucosal tissue 34. The mandrel 30 is provided with a plug 36 for sealing the first end of the mandrel 30 and a terminal port 40 for withdrawing air from the lumen of the mandrel. The terminal port 40 is connected to a vacuum generating source and a vacuum is drawn on the lumen of the mandrel 30, thus drawing air through the multiple layers of submucosal tissue while compressing the tissues against each other. A nonpermeable layer can be wrapped around the multiple layers of submucosal tissue (for example the mandrel can be placed within a plastic bag 44 that is sealed with a clamp 46 at the vacuum port) to provide a second surface that coacts with the mandrel 30 to compress the multiple layers of submucosal tissue 34 between the second surface and the mandrel 30. A vacuum is applied, generally ranging from 35.6–177.8 cm of Hg (0.49–2.46 $Kg/cm^2$) and more preferably the vacuum applied is approximately 129.5 cm of Hg (1.76 $Kg/cm^2$). Optionally a heating blanket can be placed on top of the apparatus to heat the submucosal tissue during the compression of the tissue. After compressing the submucosal tissue for a sufficient amount of time, the compressed submucosal tissue is removed from the mandrel as a unitary compliant tissue construct.

The multiple strips of submucosal tissue are typically compressed for 12–48 hours at room temperature, although heat may also be applied. For example a warming blanket can be applied to the exterior of the compressing surfaces to raise the temperature of the compressed tissue up to about 40° C. to about 50° C. The overlapped portions are usually compressed for a length of time determined by the degree of dehydration of the tissue. The use of heat increases the rate of dehydration and thus decreases the amount of time the overlapped portions of tissue are required to be compressed. Typically the tissue is compressed for a sufficient time to produce a stiff but flexible material. Sufficient dehydration of the tissue is also indicated by a increase in impedance of electrical current flowing through the tissue. When impedance has increased by 100–200 ohms, the tissue is sufficiently dehydrated and the pressure can be released.

In one preferred embodiment shown in FIG. 5a the mandrel 50 is first wrapped with a water permeable removable porous ribbon material 52 before the sheets of submucosal tissue are overlaid onto the mandrel 50. Preferably the removable ribbon material 52 comprises a water permeable material that is resistant to tearing including a porous plastic or other material that does not adhere to submucosal tissue or the mandrel. In one embodiment the porous ribbon material 52 comprises umbilical tape. The submucosal tissue layers are then layered direct on the ribbon material and dried to form a unitary tubular construct. After drying the submucosal tissue, the porous ribbon material 52 is unwrapped from the mandrel 50 by pulling on the first end 54 and second end 56 of the water permeable material 52 (See FIG. 5a) Removal of the ribbon of water permeable material 52 leaves a space between the submucosal construct and the mandrel 50, allowing for the removal of the construct from the mandrel.

In accordance with one embodiment, as shown in FIG. 5a–FIG. 5c the method of forming the construct comprises selecting a water permeable, hollow mandrel 50 of appropriate diameter, and spiral wrapping the mandrel 50 with a strip of porous ribbon material 52, for example umbilical tape. The mandrel is preferably water permeable and in one embodiment is provided with a plurality of holes. Then the desired number of wraps of a first sheet of submucosal tissue 60 are applied wherein a "wrap of submucosal tissue" is defined as a piece of submucosa tissue wrapped 360° about the mandrel. Typically 1 or 2 wraps provide a burst strength of about 1000–2000 mmHg after fabrication as described below. The first sheet of submucosal tissue 60 is applied to the mandrel 50 by a rolling motion with the desired number of layers (typically two) and an overlapped region 62

(defined by an overlap angle (θ) extending between the first edge 64 and second opposite edge 66 of the first sheet of submucosal tissue 60) to form a tube of submucosal tissue having a longitudinally extending overlapped region 62 that forms the seam of the tube (FIG. 5*b*). The overlap angle typically ranges from about 20° to about 90°, more typically about 20° to about 40°, and in one embodiment the overlap angle is about 30°. The submucosal tissue is wrapped onto the mandrel leaving the first end 54 and the second end of the water permeable material 56 exposed.

In one embodiment the seam of the wrapped tissue can be "spot welded" to ensure that the second opposite edge 66 does not come loose. In accordance with this embodiment, a Q-tip, moistened with χ% glutaraldehyde (or other cross linking or adhesive agent), is wiped along the surfaces of the portion of submucosal tissue that forms the overlapped region 62. The value for χ is about 0.1 to about 1.0%, more probably about 0.5%, but there is a relationship between the overlapped region 62 width, the glutaraldehyde concentration and number of turns that determines the bursting pressure. The layers of submucosal tissue forming the overlapped region can also be crosslinked to ensure that the end piece does not come loose by immersing the entire tube of submucosal tissue in a solution of a crosslinking agent such as glutaraldehyde. The glutaraldehyde treated tube of submucosal tissue can be optionally compressed under dehydrating conditions before overlaying the second sheet of submucosal tissue over the tube of submucosal tissue (including the use of vacuum pressing) to further bond the layers of submucosal tissue to one another.

Alternatively, the seam of the tube of submucosal tissue can be fixed by suturing the multiple layers of the tube of submucosal tissue along the overlapped region. The use of sutures negates the need for crosslinking the submucosal tissue layers of the overlapped region.

In accordance with the present invention the first sheet of submucosal tissue can be wrapped onto the mandrel in a variety of different orientations. In one embodiment the sheets have a width equal to the length of the mandrel such that a single sheet entirely covers the mandrel when wrapped 360° around the mandrel (See FIG. 5*b*).

Other wrapping techniques can be used to form the first sheet of submucosal tissue into the tube of submucosal tissue provided that no gaps exist between the seams of overlapped tissues. In one embodiment, the sheet of submucosal tissue may have a width less than the desired length of the formed tube of submucosal tissue. In this alternative embodiment a narrow sheet of submucosal tissue 80 is wound about the mandrel 82 multiple times wherein the sheet is at least partially overlapped as it is overlaid onto the mandrel, leaving no portion of the underlying mandrel exposed (See FIG. 3). The mandrel is water permeable and in one embodiment is provided with a plurality of holes 84. The amount of overlap in such partially overlapped sheets of submucosal tissue ranges between 10–60% of the width of the individual sheet and more preferably the overlapped portion is a 50% overlap. In one embodiment multiple pieces of submucosal tissue can be overlaid onto the mandrel, provided that at least a portion of each piece of submucosal tissue overlaps a portion of another piece of submucosal tissue wrapped onto the mandrel. In a further embodiment, a long, narrow sheet of submucosal tissue can be spirally wrapped on the mandrel with an overlap, followed by a spiral wrapping in the opposite direction. This will provide 4 layers of submucosal tissue to support the internal pressure. In this embodiments seams formed by overlapped sheets of submucosal tissue should overlap by 0.5 to 3 cm and more preferably from 1 to 2 cm. In the embodiments where the first sheet of submucosal tissue used to form the tube of submucosal tissue has a width less then the length of the desired tube of submucosal tissue, the seams of the tube will be fixed preferably by exposure to a crosslinking agent.

After formation of the tube of submucosal tissue a second sheet of submucosal tissue 70 is then wrapped circumferentially around the exterior surface of the formed tube of submucosal tissue 60. In one embodiment the second sheet of submucosal tissue 70 is overlaid onto the tube of submucosal tissue 60, wrapped about the tube once, and the first edge 74 and the second opposite edge 76 of the second sheet of submucosal tissue are sutured together along the length of the tube of submucosal tissue with sutures 78 without perforating the tube of submucosal tissue 60 (See FIG. 5*c*). Alternatively, the second sheet of submucosal tissue is overlaid onto the tube of submucosal tissue, wrapped about the tube at least once wherein the second opposite edge of the second sheet extends over the first edge of the second sheet of submucosal tissue and said second opposite edge of the second sheet is sutured along the length of the tube of submucosal tissue without perforating the tube of submucosal tissue.

In addition, when the second sheet of submucosal tissue is overlaid onto the tube of submucosal tissue formed from the first sheet of submucosal tissue, the second sheet can be overlaid with its abluminal surface or its luminal surface in contact with the tube of submucosal tissue. Each of these combinations of overlapping the sheets of submucosal tissue from the same or different vertebrate or organ sources will produce a unitary tubular shape submucosal tissue graft construct upon compression of at least the overlapped portions under conditions allowing dehydration of the tissue.

After the mandrel has been wrapped with the second sheet of submucosal tissue the submucosal tissue is compressed under dehydrating conditions. In one embodiment the tissue is vacuum pressed, wherein one end of the mandrel is closed and the interior of the submucosal tissue-covered mandrel is connected to a vacuum pump. The vacuum causes atmospheric pressure to compress the submucosal tissue layers, and in those embodiments that use a crosslinking agent to crosslink the submucosal tissue layers to one another, the vacuum pressing procedure causes the crosslinking agent to penetrate the entire thickness of the seam. The vacuum sealing/drying process is complete in about four hours typically.

After the sealing/drying process is complete, the first and second ends (54 and 56, respectively), of the water permeable porous ribbon material 52 (for example, umbilical tape) are grasped and pulled longitudinally. The tape unwinds easily under the submucosal tissue tube and the tube of submucosal tissue then slides off the mandrel easily. The result is a seamless tube that looks like a soda-pop straw.

In one embodiment, a tube of submucosal tissue can be prepared from one or more sheets of submucosal tissue by wrapping one or more sheets of submucosal tissue around the circumference of a mandrel, exposing the wrapped submucosal tissue to a crosslinking agent, and compressing the wrapped tissue under dehydrating conditions. The sheets of tissue can be overlaid onto the mandrel using a variety of wrapping techniques provided that no gaps exist between the seams of the overlapped sheets of submucosal tissue. In one embodiment a single sheet of submucosal tissue, having a first edge portion and a second edge portion is overlaid onto a mandrel such that the first and second edge portions of the sheet of submucosal tissue are overlapped to form a tube of submucosal tissue. In one embodiment the second edge of the sheet of submucosal tissue is extended past the first edge of the sheet of submucosal tissue wherein the first edge is substantially parallel to the second edge, to form a heterolaminate tubular construct as shown in FIG. 5b. Alternatively, a single narrow sheet of submucosal tissue can be spirally wrapped about the mandrel as shown in FIG. 3. The overlapped portions of the sheet of submucosal tissue are then contacted with a crosslinking agent. In one embodiment the entire graft construct is immersed in a cross-linking solution. One preferred cross-linking agent is glutaraldehyde, in a concentration ranging from about 0.1% to about 1% glutaraldehyde. After the overlapped layers of submucosal tissue have been treated with the crosslinking agent, the overlapped layers are compressed under dehydrating conditions. In one embodiment the overlapped layers of submucosal tissue are vacuum pressed, wherein one end of the mandrel is closed and the interior of the submucosal tissue is connected to a vacuum pump. The vacuum causes atmospheric pressure to compress the submucosal tissue layers and the vacuum pressing procedure causes the crosslinking agent to penetrate the entire thickness of the graft construct.

As indicated by the data of Example 4, tubes of submucosal tissue that have been treated with a glutaraldehyde solution of at least 1% glutaraldehyde show significant durability under pulsatile pressure tests. In addition, a tube of submucosal tissue formed by wrapping sheets of submucosal tissue into a heterolaminate tube and treated with glutaraldehyde and vacuum pressed, provides a tube of submucosal tissue with a smooth luminal surface.

It is noted that glutaraldehyde treatment of biomaterials is known to promote calcification, poor host tissue incorporation and ultimate mechanical failure of bioprostheses. To minimized the detrimental effects of glutaraldehyde treatments of biomaterials, the tubular constructs of the present invention are exposed to relatively dilute solutions of glutaraldehyde of approximately 0.1% to 1% gluteraldehdye. Glutaraldehyde treated tubular constructs formed in accordance to this present invention by treatment with a solution comprising less than 1% glutaraldehyde can be used in various non-vascular applications such as ureter and urethra replacements and as various ducts and shunts. In addition a tube of submucosal tissue, having the seams of the submucosal tissue tube sealed by a crosslinking agent, can be bonded to a second sheet of submucosal tissue to support the glutaraldehyde bonded seams. In one embodiment, the tube of submucosal tissue is rehydrated and a the second sheet of submucosal tissue is wrapped around the tube of submucosal tissue and compressed against the tube of submucosal tissue under dehydrating conditions. In one embodiment, a tube of submucosal tissue is prepared from a sheet of submucosal tissue and is contacted by a solution of glutaraldehyde (wherein the concentration of the glutaraldehyde is less than 1%, and more preferably less than 0.5%), vacuum pressed and further wrapped with a second sheet of submucosal tissue that is sutured along its longitudinal length, as shown in FIG. 5c. The second sheet of submucosal tissue in this embodiment provides sufficient support to the underlying tube of submucosal tissue such that the construct can be used in vascular applications including arterial and venous replacement, in spite of the low concentration of the crosslinking agent used to seal the tube of submucosal tissue.

In one embodiment, the method of preparing a submucosa tubular prosthesis comprises overlaying a first strip of water permeable material about the circumference of a mandrel and then overlaying a second strip of water permeable material on top of the first strip of water permeable material. A first sheet of submucosal tissue, having a first edge and a second opposite edge, is then overlaid onto the spirally wrapped material to form a tube of submucosal tissue, wherein the second opposite edge extends over the first edge to define a multi-layered overlapped region of submucosal tissue. The tube of submucosal tissue is then compressed against the surface of the mandrel under dehydrating conditions to form a tube-shaped construct. The second strip of the water permeable material is then removed from the mandrel to release the tube-shaped construct from the mandrel. The submucosal tissue layers of the overlapped region of the released tube of submucosal tissue are then sutured together, using a continuous suture, to ensure that the tube will not unravel. The tube-shaped construct is then placed back onto to the mandrel by sliding the tube over the first strip of water permeable material covering the mandrel. A second sheet of submucosal tissue, having a first edge and a second opposite edge, is then overlaid onto the tube of submucosal tissue. The first and second opposite edges of the second sheet of submucosal tissue are sutured together along the length of the tube of submucosal tissue without perforating the tube of submucosal tissue, and the multiple layers of submucosal tissue are compressed together under dehydrating conditions. The first strip of water permeable material is then removed from the mandrel to release the tubular prosthesis from the mandrel. In preferred embodiments, the sutures of the second sheet of submucosal tissue do not overlap the sutures formed in the overlapped region of the tube of submucosal tissue.

The multi-laminate tissue graft constructs can be formed to have substantially isotropic properties. These substantially isotropic (pseudoisotropic) grafts are prepared from at least two sheets of intestinal submucosal tissue delaminated from both the tunica muscularis and the luminal portion of the tunica mucosa of a warm blooded vertebrate. Each of the sheets of intestinal submucosal tissue are characterized as having a longitudinal axis corresponding to the predominant orientation of the collagen fibers in the submucosal tissue sheets. The method of forming the pseudoisotropic graft constructs comprises locating a first sheet of submucosal tissue on a the mandrel, overlaying said first sheet with at least one additional sheets of submucosal tissue so that the longitudinal axes of each individual sheet of submucosal tissue forms an angle of about 90° with the longitudinal axis of the other sheet of submucosal tissue forming the heterolaminate graft.

Biological tissue implants or constructs produced according to the present invention overcome the problem of leakage of fluid around suture holes of sewn biological tissues. The construction of two concentric tubes of submucosal tissue wherein the sutured seams of the tube of the two tube are offset relative to each other followed by adhering the two tubes of submucosal tissue together ensures that the suture holes will not leak in the formed prothesis. Furthermore the embodiments that utilize a crosslinking treatment to seal the seam of the first tube clearly do not have any perforations formed in the tube wall and thus will not leak. The construct tubes produced according to the present invention exhibit an essentially seamless tube which will not leak fluid or require extra precautions associated with fluid efflux. This property is particularly important when the construct is to be used as a vascular graft, ureter replacement or as a shunt. The construct can be further manipulated (i.e., cut, folded, sutured, etc.) to suit various medical applications where the submucosal material of the present invention is required.

Other features and aspects of this invention will be appreciated by those skilled in the art upon reading and understanding this specification. Such features, aspects and expected variations and modifications are clearly within the scope of this invention.

EXAMPLE 1

Preparation of Tubular Submucosal Tissue Graft Constructs

In one embodiment, the method of forming the construct comprises selecting a water permeable, hollow mandrel of appropriate diameter and spiral wrapping the mandrel with umbilical tape. Then the desired number of wraps of submucosal tissue are applied wherein a "wrap of submucosal tissue" is defined as a piece of submucosa tissue wrapped 360° about the mandrel. Typically 1 or 2 wraps provide a burst strength of about 1000–2000 mmHg after fabrication as described below.

A sheet of submucosal tissue is placed on a smooth flat surface with the mucosal side up. The tape-wrapped mandrel is laid on it with the long axis parallel to the long axis of the submucosal tissue. A razor blade is then used to cut the submucosal tissue parallel to the axis of the mandrel to form a linear edge for the submucosal tissue. The submucosal tissue is applied to the mandrel by a rolling motion with the desired number of layers (typically two) and an overlap region (defined by an overlap angle ($\theta$) of about 30 degrees extending between the two lateral edges of the submucosal tissue) forms a tube of submucosal tissue having a longitudinally extending seam.

After the mandrel has been completely wrapped, one end of the mandrel is closed and the interior of the submucosal tissue-covered mandrel is connected to a vacuum pump. The vacuum causes atmospheric pressure to compress the submucosal tissue layers and speeds the dehydration of the submucosal tissue. The vacuum sealing/drying process is complete in about four hours typically.

After the drying/sealing treatment, the ends of the umbilical tape are grasped and pulled longitudinally. The tape unwinds easily under the submucosal tissue tube which then slides off the mandrel easily. The result is a seamless tube that looks like a soda-pop straw.

Other sealant types, concentrations and wrapping techniques can be used. For example, spiral winding of a long, narrow strip of submucosal tissue on the mandrel with an overlap is an option, followed by a spiral wrapping in the opposite direction is another. This will provide 4 layers of submucosal tissue to support the internal pressure. This double helix could be combined with the wrap technique shown in FIG. 3. In accordance with the present invention the submucosal tissue can be wrapped onto the mandrel in a variety of different orientations. The one limitation is that no gaps should exist between the seams of overlapped tissues. In preferred embodiments seams formed by overlapped strips of submucosal tissue should overlap by 0.5 to 3 cm and more preferably from 1 to 2 cm.

EXAMPLE 2

Spot Welding of Submucosal Tissue Seams

In one embodiment the seam of the wrapped tissue can be "spot welded" to ensure that the end piece does not come loose. In accordance with one embodiment the seam is spot welded with a crosslinking agent such a glutaraldehyde. A Q-tip, moistened with $\chi\%$ glutaraldehyde (or other cross linking or adhesive agent), is wiped along the overlap which is the seam. The value for $\chi$ is about 0.1 to about 1.0%, more probably about 0.5%, but there is a relationship between the seam width, the glutaraldehyde concentration and number of turns that determines the bursting pressure. Alternatively the seam can be spot welded through the use of a laser.

In another embodiment the seam of submucosal tube can be thermally spot welded to further seal the seam bond the tissue into a unitary tube of submucosa. There are four factors that control the quality of a thermal spot weld applied to submucosal tissue: 1) temperature, 2) force, 3) time of force application, and 4) the shape of the thermal welding tool. A pointed tool makes a weld with a hole. A flat tip makes no hole and a tip with a radius can make a small hole.

Using a small soldering iron with a temperature-calibrated tip, submucosal tissue can be melted in discrete locations to form a "weld" point between two pieces of submucosal tissue. By placing a specimen of submucosal tissue on a glass plate (to avoid heat sinking) the warmed tip is applied to the submucosal tissue to determine the temperature and time of application necessary to melt the tissue. Studies have been conducted on 1-cm wide strips of submucosal tissue overlapped by 1-cm to determine the number of thermal spot welds required to hold two pieces of submucosal tissue together. 5 spot welds in the 1×1 cm overlapping area produces a weld that is stronger than the force needed to break a single thickness 1-cm wide strip. A pointed tip produces a small weld with a hole; therefore the challenge is to identify the parameters that produce the strongest weld with the smallest hole.

To optimize the spot welding conditions, the following experiments are conducted. 1 cm wide and 10 cm long pieces of submucosal tissue are utilized and fifty specimens will be fabricated and tested with three of the four variables (temperature, time, force and tip shape) being held constant and the one varied. In these first studies, the pointed tip will be used. Then the studies will be repeated with the 0.5 mm radius tip, then with a 1 mm diameter flat tip. The result will be the recipe for the strongest weld with the smallest hole, being measured with a microscope. We will also determine the break strength of selected specimens using the MTS machine.

b) Animal Model

The weanling rat model will be used to investigate the host response to spot welded submucosal tissue strips. Anesthesia will be induced and maintained with metafane administered via face mask. The ventral abdomen will be clipped and prepared for aseptic surgery. Longitudinal skin incisions will be made in each abdominal quadrant. Then bilateral subcutaneous pockets will be created in the subcutis of each rat by blunt dissection. One 1 $CM^2$ test specimen will be placed subcutaneously within each pocket and secured in position with one 5-0 polypropylene suture to the underlying fascia. Skin incisions will be closed with a simple interrupted suture pattern with 5-0 polypropylene. Twenty-four rats will be used in this study.

After the elapsed time, euthanasia will be performed with intracardiac potassium chloride (at 1, 2, 4 and 8 weeks post-implantation).

c) Morphologic Analyses

Samples removed for morphologic evaluation will be fixed in Trump's fixative for 24 hours, then placed in a phosphate buffer. Specimens for light microscopy will be embedded in paraffin and sectioned to 2–3 $\mu$m. Sections will be stained with hematoxylin and eosin (H&E) for overall morphology and VonKossa stain for calcification evaluation.

EXAMPLE 3

Submucosal tissue Tube Fabrication and Testing

The goal for this study is to produce grafts with an outer diameter of 5.0 mm. A multihole hollow mandrel of 4 mm diameter is spiral wrapped with non-overlapping umbilical tape. Then the two and one-half wraps of submucosal tissue are applied to form a tube of submucosal tissue and the overlapped portion are fixed with glutaraldehyde in one group and with sutures in another group. A second sheet of submucosal tissue is then wrapped about the tube of submucosal tissue and the opposing ends of the second sheet of submucosal tissue are sutured together. After wrapping, one end of the mandrel is connected to a vacuum pump and the other end of the mandrel is closed. The resulting vacuum in the mandrel causes atmospheric pressure to press the layers of submucosal tissue together firmly and draws the moisture out of the submucosal tissue, which requires about 24 hours.

After drying the layers of submucosal tissue the ends of the umbilical tape are grasped and pulled longitudinally. The tape unwinds evenly under the submucosal tissue tube which then slides off the mandrel easily.

e) Static Testing

Prior to burst testing, each submucosal tissue graft will be soaked in 0.9% saline at 37° C. for 24 hours. The objective of this procedure is to determine the durability of the seams.

To determine the burst strength one end of the tubular submucosal tissue graft is mounted to a fitting which will be used to apply air pressure. The other end of the tubular submucosal tissue graft is closed with a suture and increasing air pressure is applied. A continuous recording of pressure versus time allows exact identification of the burst pressure. Our target is a burst pressure of 1000 mmHg or more. A successful fabrication technique is one that produces a burst, (at any pressure), without delamination. Tubular submucosal tissue graft that pass this static test will proceed to pulsatile testing.

f) Pulsatile Testing

The critical period for a tubular submucosal tissue graft is the first few weeks following implantation when it is in the initial stage of remodeling and is exposed to warm blood with a static (diastolic) and pulsatile pressure. During this time it is essential to know if the graft will retain its strength during early remodeling. Accordingly we will perform pulsatile pressure testing with the graft constructs in saline at 37° C. A pulsating pressure of 200/150 mmHg will be used with a frequency of 1/sec. Testing will continue for 2 weeks after which the graft will be static burst tested.

EXAMPLE 4

Pulsatile Testing of Tubes of Submucosal Tissue

To test the durability of submucosa derived tubular constructs fabricated from sheets of submucosal tissue in accordance with the present invention, a pulsatile testing method was developed. A pulsatile pressure pump was assembled which supplies pressure pulses of adjustable intensity at 4.5 Hz. The working fluid for the system is sterile water. The pressure is supplied to the formed submucosal tissue tubular graft constructs, which are attached to the outlet of the pump. The tubes are immersed in water at 37° C. to simulate physiological conditions. Typically, the pulsatile testing system is run at pressures of 150/50 mmHg or 400/200 mmHg. A drop in applied pressure is indicative of failure of the tissue graft.

Results of Testing of Submucosa Derived Tubes

Glutaraldehyde-treated Tubes of Submucosal Tissue

Hydrated small intestinal submucosal tissue (2.5 turns) was wrapped around a multi-holed, hollow mandrel and immersed in a dilute glutaraldehyde (GA) solution and vacuum dried as described earlier. These GA-treated tubes of submucosal tissue were then tested on the pulsatile testing machine.

The grafts that were treated with ≧1% GA solution (w/w) showed significant durability under pulsatile pressure (400/200), surviving in excess of 5.5 million pulsatile cycles. Tubes treated with <1% GA solution (w/w) were significantly less durable, lasting less than five hundred thousand cycles under similar conditions. Accordingly, treating the tubes of submucosal tissue with a 1% (w/w) or higher GA solution provided a unitary tube of submucosal tissue having the desired durability to pulsatile pressure.

Non-treated, Hand-sutured Tubes of Submucosal Tissue

Hydrated small intestinal submucosal tissue was wrapped around a multi-holed, hollow mandrel, vacuum dried, the seam sutured and then wrapped with an additional layer of small intestinal submucosal tissue and hand sutured along its length as shown in FIGS. 5b and 5c. These untreated, hand-sutured tubes were then tested on the pulsatile testing machine.

The results of these tests showed the hand-sutured tubes survived in excess of 6 million pulsatile cycles, the test being intentionally discontinued and the durability limit is yet to be ascertained.

What is claimed is:

1. A unitary multi-layered submucosal tissue prosthesis comprising
    a first sheet of submucosal tissue, having a first edge and a second opposite edge, formed in the shape of a tube of submucosal tissue, wherein the second opposite edge of the first sheet extends over the first edge of the first sheet to define a multiple layered overlapped region of submucosal tissue, wherein the submucosal tissue layers in the overlapped region are fixed to one another; and
    a second sheet of submucosal tissue, having a first edge and a second opposite edge, wherein said second sheet is in adherent contact with the tube of submucosal tissue and the first edge and second opposite edge of the second sheet are sutured together along the length of the tube of submucosal tissue without perforating the underlying tube of submucosal tissue.

2. The prosthesis of claim 1 wherein the tube of submucosal tissue is formed from the first sheet of submucosal tissue such that the first and second opposite edges of the first sheet of submucosal tissue are substantially parallel to one another.

3. The prosthesis of claim 2 wherein the tube of submucosal tissue comprises two layers of submucosal tissue and the multiple overlapped region comprises three layers of submucosal tissue.

4. The prosthesis of claim 1 wherein the multiple layers of submucosal tissue in the overlapped region are fixed to one another by treatment with a crosslinking agent.

5. The prosthesis of claim 4 wherein the tube of submucosal tissue and the second sheet of submucosal tissue are fused to one another by compressing the submucosal tissue under conditions conducive to dehydration of the tissue.

6. The prosthesis of claim 4 wherein the crosslinking agent is glutaraldehyde.

7. The prosthesis of claim 1 wherein the multiple layers of submucosal tissue in the overlapped region are fixed to one another by sutures, and the overlapped region is offset from the sutures formed in the second sheet of submucosal tissue.

8. The prosthesis of claim 7 wherein the tube of submucosal tissue and the second sheets of submucosal tissue are fused to one another by compressing the submucosal tissue under conditions conducive to dehydration of the tissue.

9. The prosthesis of claim 1 wherein the submucosal tissue comprises intestinal tissue submucosa delaminated from both the abluminal muscle layers and at least the luminal portion of the tunica mucosa of a warm-blooded vertebrate.

10. The prosthesis of claim 1 wherein the tube of submucosal tissue is formed with the abluminal surface of the sheet of submucosal tissue on the exterior of the tube.

11. A unitary multi-layered submucosal tissue prosthesis comprising
   a first sheet of submucosal tissue, having a first edge and a second opposite edge, formed in the shape of a tube of submucosal tissue, wherein the second opposite edge of the first sheet extends over the first edge of the first sheet to define a multiple layered overlapped region of submucosal tissue, wherein the submucosal tissue layers in the overlapped region are fixed to one another; and
   a second sheet of submucosal tissue, having a first edge and a second opposite edge, wherein said second sheet is in adherent contact with the tube of submucosal tissue and the second opposite edge of the second sheet extends over the first edge of the second sheet and is sutured to the second sheet of submucosal tissue without perforating the underlying tube of submucosal tissue.

12. The prosthesis of claim 11 wherein the tube of submucosal tissue is formed from the first sheet of submucosal tissue such that the first and second opposite edges of the first sheet of submucosal tissue are substantially parallel to one another.

13. The prosthesis of claim 11 wherein the multiple layers of submucosal tissue in the overlapped region are fixed to one another by treatment with a crosslinking agent.

14. The prosthesis of claim 13 wherein the tube of submucosal tissue and the second sheet of submucosal tissue are fused to one another by compressing the submucosal tissue under conditions conducive to dehydration of the tissue.

15. The prosthesis of claim 13 wherein the crosslinking agent is glutaraldehyde.

16. The prosthesis of claim 11 wherein the multiple layers of submucosal tissue in the overlapped region are fixed to one another by sutures, and the overlapped region is offset from the sutures formed in the second sheet of submucosal tissue.

17. The prosthesis of claim 11 wherein the tube of submucosal tissue and the second sheets of submucosal tissue are fused to one another by compressing the submucosal tissue under conditions conducive to dehydration of the tissue.

18. The prosthesis of claim 11 wherein the submucosal tissue comprises intestinal tissue submucosa delaminated from both the abluminal muscle layers and at least the luminal portion of the tunica mucosa of a warm-blooded vertebrate.

19. A method of preparing a tubular prosthesis from sheets of submucosal tissue, said method comprising:
   selecting a mandrel having a predetermined diameter;
   overlaying a first sheet of submucosal tissue, having a first edge and a second opposite edge, onto the mandrel to form a tube of submucosal tissue, wherein the second opposite edge of the first sheet of submucosal tissue extends over the first edge of the first sheet of submucosal tissue to define a multi-layered overlapped region of submucosal tissue;
   fixing the submucosal tissue layers in the overlapped region to one another;
   overlaying a second sheet of submucosal tissue, having a first edge and a second opposite edge over the tube of submucosal tissue;
   suturing the second opposite edge of the second sheet of submucosal tissue to the overlaid second sheet of submucosal tissue along the length of the tube of submucosal tissue without perforating the tube of submucosal tissue; and
   compressing the tube of submucosal tissue and the second sheet of submucosal tissue against the mandrel under dehydrating conditions.

20. The method of claim 19 further comprising the step of overlaying a strip of water permeable material onto the mandrel before the first sheet of submucosal tissue is overlaid onto the mandrel, wherein after formation of the tubular prosthesis, the strip of water permeable material is removed from the mandrel to assist in the release of the tubular prosthesis from the mandrel.

21. The method of claim 20 wherein the first and second opposite edges of the second sheet of submucosal tissue are sutured together along the length of the tube of submucosal tissue without perforating the tube of submucosal tissue.

22. The method of claim 20 wherein the second opposite edge of the second sheet extends over the first edge of the second sheet of submucosal tissue and said second opposite edge of the second sheet is sutured along the length of the tube of submucosal tissue without perforating the tube of submucosal tissue.

23. A method of preparing a tubular prosthesis from sheets of submucosal tissue, said method comprising:
   selecting a mandrel having a predetermined diameter;
   overlaying a first sheet of submucosal tissue, having a first edge and a second opposite edge, onto the strip of water permeable material to form a tube of submucosal tissue, wherein the second opposite edge of the first sheet of submucosal tissue extends over the first edge of the first sheet of submucosal tissue to define a multi-layered overlapped region of submucosal tissue;
   contacting the tube of submucosal tissue with a solution containing a crosslinking agent;
   overlaying a second sheet of submucosal tissue, having a first edge and a second opposite edge over the tube of submucosal tissue;
   suturing the first and second opposite edges of the second sheet of submucosal tissue together along the length of the tube of submucosal tissue without perforating the tube of submucosal tissue; and
   compressing the tube of submucosal tissue and the second sheet of submucosal tissue against the mandrel under dehydrating conditions.

24. The method of claim 23 further comprising the step of overlaying a strip of water permeable material onto the mandrel before the first sheet of submucosal tissue is overlaid onto the mandrel, wherein after formation of the tubular prosthesis, the strip of water permeable material is removed from the mandrel to assist in the release of the tubular prosthesis from the mandrel.

25. The method of claim 24 further comprising the step of compressing the tube of submucosal tissue against the mandrel under conditions conducive to dehydration of the tissue after the tube of submucosal tissue is contacted with the crosslinking agent and before the second sheet of submucosal tissue is overlaid onto the tube of submucosal tissue.

26. The method of claim 24 wherein the crosslinking solution comprises about 0.1 to about 1.0% glutaraldehyde.

27. The method of claim 24 wherein said mandrel is a hollow porous tube having a luminal space, and the step of compressing said biological tissue is accomplished by drawing a vacuum on the lumen of the mandrel.

28. The method of claim 24 wherein the tube of submucosal tissue and the second sheet of submucosal tissue is heated during the step of compressing the tube of submucosal tissue and the second sheet of submucosal tissue.

29. The method of claim 24 wherein the step of compressing the tube of submucosal tissue and the second sheet of submucosal tissue is accomplished by a compression chamber.

30. A method of preparing a tubular prosthesis from sheets of submucosal tissue, said method comprising:

selecting a mandrel having a predetermined diameter;

overlaying a first sheet of submucosal tissue, having a first edge and a second opposite edge, onto the water permeable material to form a tube of submucosal tissue, wherein the second opposite edge of the first sheet of submucosal tissue extends over the first edge of the first sheet of submucosal tissue to define a multi-layered overlapped region of submucosal tissue;

compressing said tube of submucosal tissue against the mandrel under dehydrating conditions;

suturing the layers of the overlapped region together;

overlaying a second sheet of submucosal tissue, having a first lateral edge and a second opposite edge, over the tube of submucosal tissue;

suturing the first and second opposite edges of the second sheet of submucosal tissue together along the length of the tube without perforating the tube of submucosal tissue; and compressing the tube of submucosal tissue and the second sheet of submucosal tissue against the mandrel under dehydrating conditions.

31. The method of claim 30 further comprising the step of overlaying a strip of water permeable material onto the mandrel before the first sheet of submucosal tissue is overlaid onto the mandrel, wherein after formation of the tubular prosthesis, the strip of water permeable material is removed from the mandrel to assist in the release of the tubular prosthesis from the mandrel.

32. The method of claim 31 wherein said mandrel is a hollow porous tube having a luminal space, and the step of compressing said biological tissue is accomplished by drawing a vacuum on the lumen of the mandrel.

33. The method of claim 31 wherein the tube of submucosal tissue and the second sheet of submucosal tissue is heated during the step of compressing the tube of submucosal tissue and the second sheet of submucosal tissue.

34. The method of claim 31 wherein the step of compressing the tube of submucosal tissue and the second sheet of submucosal tissue is accomplished by a compression chamber.

35. A method of forming a unitary heterolaminate tubular construct from a sheet of submucosal tissue said method comprising overlaying a sheet of submucosal tissue having a first edge portion and a second edge portion onto a mandrel, wherein the first and second edge portions of said sheet of submucosal tissue are overlapped to form a tube of submucosal tissue;

contacting the overlapped first and second edge portions with a crosslinking agent; and compressing the overlapped first and second edge portions under dehydrating conditions.

36. The method of claim 35 wherein the overlapped first and second portions are compressed by vacuum pressing.

37. The method of claim 36 wherein the crosslinking agent is glutaraldehyde.

* * * * *